United States Patent
Yokota et al.

(10) Patent No.: US 7,219,997 B2
(45) Date of Patent: May 22, 2007

(54) METHOD AND APPARATUS FOR THREE DIMENSIONALLY DISPLAYING EYEGROUND AND MEASURING COORDINATES THEREOF

(75) Inventors: Hideo Yokota, Wako (JP); Akitake Makinouchi, Wako (JP); Hiroo Yabe, Wako (JP)

(73) Assignee: Riken, Saitama (JP)

( * ) Notice: Subject to any disclaimer, the term of this patent is extended or adjusted under 35 U.S.C. 154(b) by 541 days.

(21) Appl. No.: 10/606,843

(22) Filed: Jun. 27, 2003

(65) Prior Publication Data

US 2004/0080712 A1    Apr. 29, 2004

(30) Foreign Application Priority Data

Jun. 28, 2002    (JP)    ............... 2002-189265

(51) Int. Cl.
*A61B 3/10*    (2006.01)
(52) U.S. Cl. ........................... 351/212; 351/246
(58) Field of Classification Search ................ 351/200, 351/205, 206, 246, 212; 382/285
See application file for complete search history.

(56) References Cited

U.S. PATENT DOCUMENTS

| | | | | |
|---|---|---|---|---|
| 4,261,367 A | * | 4/1981 | Freese | .................. 600/452 |
| 4,564,018 A | * | 1/1986 | Hutchison et al. | .......... 600/452 |
| 5,353,073 A | * | 10/1994 | Kobayashi | ................... 351/221 |
| 5,369,736 A | * | 11/1994 | Kato et al. | .................... 345/582 |
| 5,649,032 A | * | 7/1997 | Burt et al. | ................... 382/284 |
| 5,766,016 A | * | 6/1998 | Sinclair et al. | ............. 434/262 |
| 5,943,116 A | * | 8/1999 | Zeimer | ....................... 351/221 |
| 6,192,269 B1 | * | 2/2001 | Okumura et al. | ........... 600/479 |
| 6,454,410 B1 | * | 9/2002 | Berger et al. | ............... 351/206 |
| 6,714,672 B1 | * | 3/2004 | Berestov et al. | ............ 382/154 |
| 6,754,400 B2 | * | 6/2004 | Florin et al. | ................ 382/285 |
| 2004/0246440 A1 | * | 12/2004 | Andino et al. | .............. 351/177 |

FOREIGN PATENT DOCUMENTS

JP    2002-034925    2/2002

* cited by examiner

*Primary Examiner*—Hung Xuan Dang
(74) *Attorney, Agent, or Firm*—Griffin & Szipl, P.C.

(57) ABSTRACT

Presented are a shape measuring step (A) in which the size L of an eyeball 1 and the shape R of the eyeground 2 are measured, an eyeball setting step (B) for setting an eyeball template 3, an eyeground image taking step (C) for taking images of the eyeground including superimposed portions d by shifting the imaging positions, a parameter setting step (D) for obtaining an eyeball parameter g that represents the positional relationship between the eyeground and images, an image pasting step (F) for pasting a number of images on the eyeball template, and a three dimensional image displaying step (H) for displaying three dimensional eyeground images 5 on the eyeball template on a display device 16.

7 Claims, 8 Drawing Sheets

Fig.1

PRIOR ART

Section of optical system in an eyeball

Coordinate chart of retina

Fig.6

Projection from planar image to eyeground

Fig.7

Change template within projected image

Fig.8A

Example of imaging in different directions

Fig.8B

Example of imaging in different directions

Fig.9

Example of considering crystalline lens

Fig.10

Eyeground photo image (XY image)　　Section image (YZ image)

Instructing special range

METHOD AND APPARATUS FOR THREE DIMENSIONALLY DISPLAYING EYEGROUND AND MEASURING COORDINATES THEREOF

This application claims priority of Japanese Application No. JP-2002-189265, filed on Jun. 28, 2002. The entire disclosure of the above application is hereby incorporated by reference.

BACKGROUND OF THE INVENTION

1. Technical Field of the Invention

The present invention relates to methods and apparatus for displaying an eyeground three dimensionally and measuring its coordinates from photos of the eyeground.

2. Description of the Related Art

An eyeground means the inner portion of an eyeball, and is one of the few portions of a human body wherein blood vessels and nerves can be directly observed. Conventionally, dedicated eyeground cameras have been used to observe the eyeground and diagnose abnormalities in blood vessels, retinas, tumors, etc.

The eyeground camera illuminates the interior of an eye through a pupil of a patient, and at the same time the camera takes a picture of part of the eyeground on photo film or CCD. However, the field of view of the eyeground camera is narrow at about 50 degrees, so even a specialized physician cannot easily make a precise diagnosis using a photo.

Therefore, a number of eyeground photos are connected according to conventional practice. That is, because the imaging range of an eyeground camera is narrow, photos taken in a number of directions such as center, upper, lower, left, and right directions are connected together, and the entire eyeground is diagnosed. Such connecting work is done not only manually but also semi automatically using an image processing method. In addition, eyeground cameras connected to computers have been developed for electronic clinical cards and video images can be filed.

However, because the eyeground is spherical and a photo of it is a projection of part of the eyeground on a plane, photos taken are not continuous and cannot be precisely connected.

Eyeground photos connected as described above consist of planes developed from the spherical eyeground, so only a specialist physician can precisely diagnose such photos, applying extensive expertise of the construction of an eyeball, and a physician without specialized knowledge or a patient cannot understand the images.

Furthermore, even if a specialized physician can diagnose an abnormality in blood vessels, retinas, tumors, etc. at the eyeground, images on eyeground photos have already been deformed, therefore, sizes and positions of blood vessels, retina detachment areas, etc. can neither be quantified as data nor be used as time series data or as an epidemic database.

To solve the aforementioned problems, "Methods and apparatus for recovering three dimensional patterns of an eyeground by superimposing eyeground images taken in multiple directions" (unexamined Japanese patent publication No. 2002-34925) has already been proposed.

Figure 1:
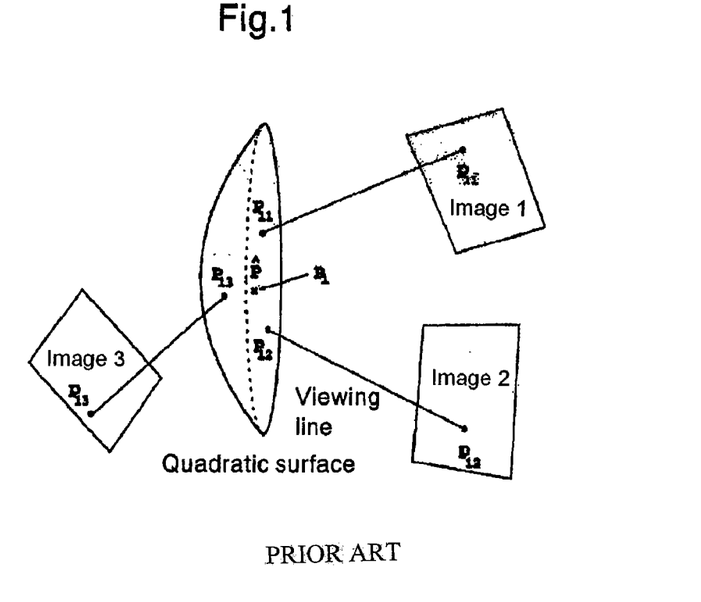
FIG. 1 is a schematic view of the method of superimposing eyeground images in the prior art.

According to this proposal, the lens of a living eye is modeled with a single lens, wherein the shape of the eyeground is regarded to be substantially a sphere; then, an image of the sphere taken through the single lens lies on a quadratic surface, and it can be assumed that the camera has taken pictures of the quadratic surface from various directions. Consequently, as shown schematically in FIG. 1, a number of unique points commonly contained in a number of eyeground photos are superimposed on the quadratic surface, thus camera positions and poses, when the shape of the quadratic surface and pictures were taken and estimated, the parameters of a single lens are obtained from the shape of the quadratic surface, and the shape of the eyeground can be reproduced.

Nevertherless, actual sizes and shapes of eyeballs vary by person, and it is known that if a person who is very near or far sighted in particular, the eyeballs deform from a precise sphere. Therefore, if the lens of a living eye is modeled with a single lens and the shape of the eyeground is regarded to be substantially a sphere, in the case of a deformed eye ball, if any, the reproduced eyeground differs from the actual eyeground, so the fact that the reproduced eyeground cannot be used for precision diagnostics or a database of eyeground data, is a problem.

According to the above mentioned method, if an eye ball is deformed significantly, images cannot be superimposed on a virtual quadratic surface. As a result, camera positions and poses when each image is photographed can no longer be estimated, so parameters for a single lens also cannot be obtained, and even the shape of the eyeground might not be reproducible.

SUMMARY OF THE INVENTION

The present invention aims to solve the aforementioned problems. More explicitly, an object of the present invention is to provide methods and apparatus that even if an eye ball is deformed from being a precise spherical surface, a three dimensional image of the eyeground can be accurately reproduced, and quantitative data on sizes and positions of abnormal blood vessels, retina detachment, tumors, etc. can be created from the above mentioned three dimensional image, and the data can be used as time dependent data of the patient and for an epidemic database by cubicly displaying the eyeground and measuring coordinates three dimensionally.

The present invention provides methods and apparatus for three dimensionally displaying an eyeground and measuring the coordinates of the eyeground, and is composed of a shape measuring step (A) for measuring the size L of an eye ball and the shape R of the eyeground, an eyeball setting step (B) for setting an eyeball template according to the measured size and shape, an eyeground image taking step (C) for taking images of the eyeground including the superimposed portion d by shifting the imaging position by a predetermined amount h, a parameter setting step (D) for obtaining eyeball parameter g, which represents the positional relationship between the eyeground and a image from the position H of the superimposed portion on the image, an image pasting step (F) for pasting a number of images on the eyeball template according to the eyeball parameter, and a three dimensional image display step (H) for displaying the three dimensional eyeball image on the eyeball template, onto a display device.

According to the above mentioned methods of the present invention, because in the shape measuring step (A), the measuring device measures the size L of the eyeball (the length from the surface of the cornea to the eyeground) and the shape R of the eyeground (radius of curvature at the eyeground), even if the eyeball is deformed from being a perfect sphere, an accurate eyeball template can be set in the eyeball setting step (B).

Because the imaging position is shifted by a predetermined amount h and an eyeground including the superimposed portion d is photographed in the eyeground image taking step (C), an eyeball parameter g that represents the positional relationship between the eyeground and the image (for example, CCD of the imaging device) can be obtained from the position H of the superimposed portion on the image in the parameter setting step (D).

Because imaging positions are shifted each time by a predetermined amount h and a number of eyeground areas including superimposed portions d are photographed, and the number of images are pasted on the eyeball template based on the eyeball parameter g in the image pasting step (F), a three dimensional image of the eyeground can be precisely produced, so this image is displayed in the display device in the three dimensional image displaying step (H) to help specialized physicians and patients understand the situation.

According to a preferred embodiment of the present invention, there is an image/position recording step (E) in which an image photographed in the aforementioned eyeground image taking step (C) and the positional relationship between the eyeball and the imaging device related to the image are recorded in a storage medium.

This method uses the storage medium to store time dependent data of the patient and provide for an epidemic database.

The present invention also provides an image positioning step (G) in which eyeground images are positioned within the eyeground surface according to the respective points at the aforementioned superimposed portions d.

Positions of eyeground images can be precisely matched using the respective points of papillae, blood vessels, nerves, etc. on the eyeground.

According to another preferred embodiment of the present invention, there are a characteristic portion indicating step (J) for indicating a characteristic portion on the above mentioned three dimensional eyeground image displayed in the display device, a three dimensional coordinate defining step (K) for obtaining three dimensional coordinates of an indicated characteristic portion, a characteristic portion measuring step (L) for measuring the size of the characteristic portion, and a data saving step (M) for saving measured data in the recording medium.

A characteristic portion on a three dimensional eyeground image displayed on the display device is indicated in the characteristic portion indicating step (J), thereby the three dimensional coordinates of the indicated characteristic portion can be obtained in the three dimensional coordinate defining step (K); in addition, the size of the characteristic portion can be measured in the characteristic portion measuring step (L); therefore, based on the three dimensional image, sizes and positions of pathologic locations such as abnormal blood vessels, retina detachment, and tumors can be converted into quantitative data.

In addition, measured data are saved in the storage medium in the data saving step (M), thereby the data can be utilized as time dependent data of the patient and as an epidemic database.

The present invention also provides a computer program to execute the above mentioned methods, and a storage medium that stores the program that the computer can read.

Using this program and the storage medium, the aforementioned methods can be implemented with the computer.

Other objects and advantages of the present invention are revealed in the following description referring to the attached drawings.

DESCRIPTION OF THE PREFERRED EMBODIMENTS

The present invention is described in more detail referring to the drawings.

In each drawing, common portions are identified with the same numbers, and no duplicate description is given.

Figure 2A:
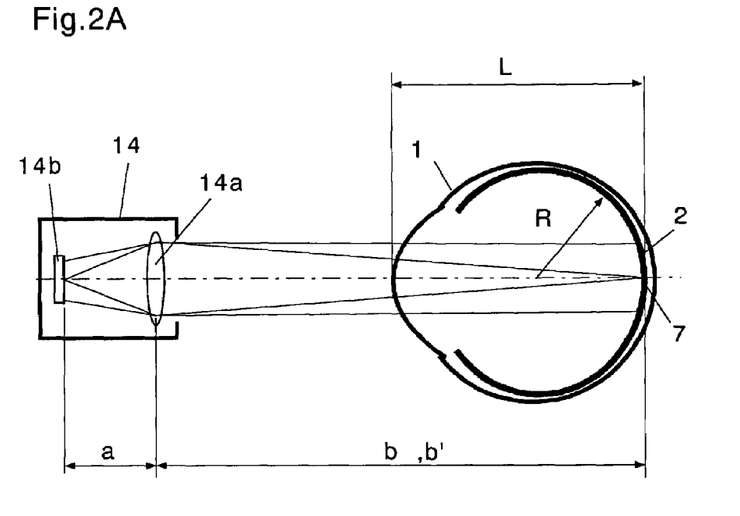
FIGS. 2A and 2B show the positional relationship between an eyeball 1 and a imaging device 14.
Figure 2B:
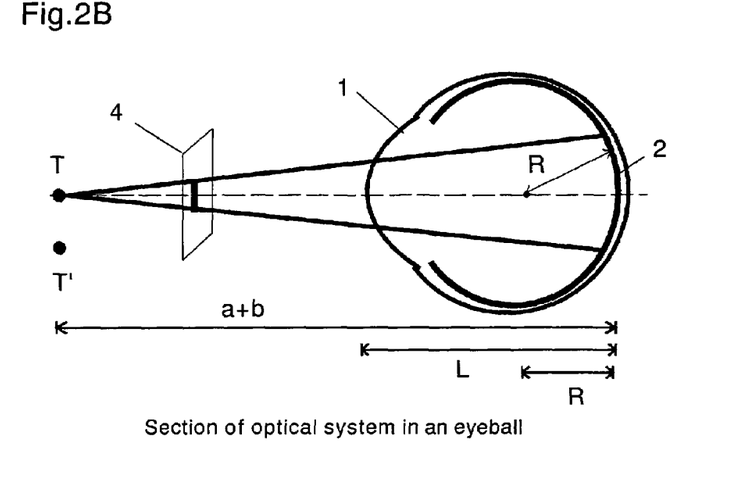

FIGS. 2A and 2B show the positional relationship between the eyeball 1 and the imaging device 14.

FIG. 2A is a view that also shows the optical system of the imaging device 14, and FIG. 2B is a schematic view omitting the optical system of the imaging device 14. The principles of the present invention are described using these figures.

In FIG. 2A, 14a represents the lens of the imaging device 14 (eyeground camera), and 14b is a CCD that records images. When the imaging device 14 takes a picture of the eyeground, the following equation (1) is known to hold by omitting the presence of the eyeball 1.

$$a^{-1}+b^{-1}=f^{-1} \tag{1}$$

Where f is the focal distance of the lens 14a.

Because the eyeball 1 has a refractive index n, which is substantially constant, when the size L of the eyeball 1 (length from the surface of cornea to the eyeground) is known, the equation (2) is valid, where b in equation (1) is replaced with b' modified from b by the size L of eyeball 1 and the refractive index n.

$$a^{-1}+b'^{-1}=f^{-1} \tag{2}$$

From equation (2), the ratio of the size of the subject (eyeground) and the size of an image 4 on the CCD is shown by equation (3), from equation (2).

$$\text{Subject: Image}=b':a \tag{3}$$

In the above, the subject is eyeground 2, which is normally a sphere. The image 4 on the CCD lies on a plane. If the patient is very near or far sighted, the eyeball 1 deforms from being a perfect sphere, but the size L of eyeball 1 (length from the surface of the cornea to the eyeground) and the shape R of eyeground 2 (radius of curvature at the eyeground) can be measured using a measuring device 12.

Therefore, if the image 4 and the relationship between the eyeball 1 and the imaging device 14 related to the image (the aforementioned a, b, L, and R) are known accurately and the image is pasted on the eyeground of the eyeball concerned, a three dimensional eyeground image (5) can be displayed on the display device of the computer.

Figure 9:
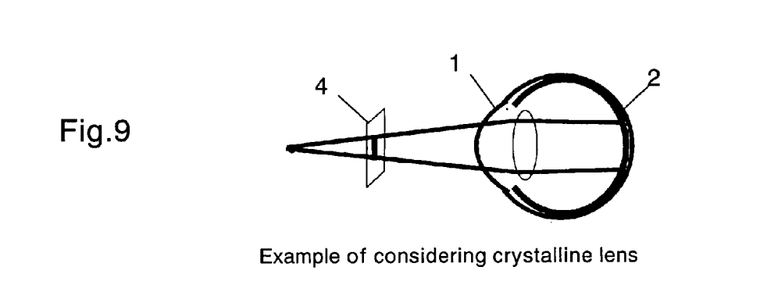
FIG. 9 is the view of an example taking crystalline lens.

If the crystal lens is taken into account as shown in FIG. 9, the above mentioned equations (2) and (3) should be modified by setting a function that considers the shape of the lens.

Figure 3:
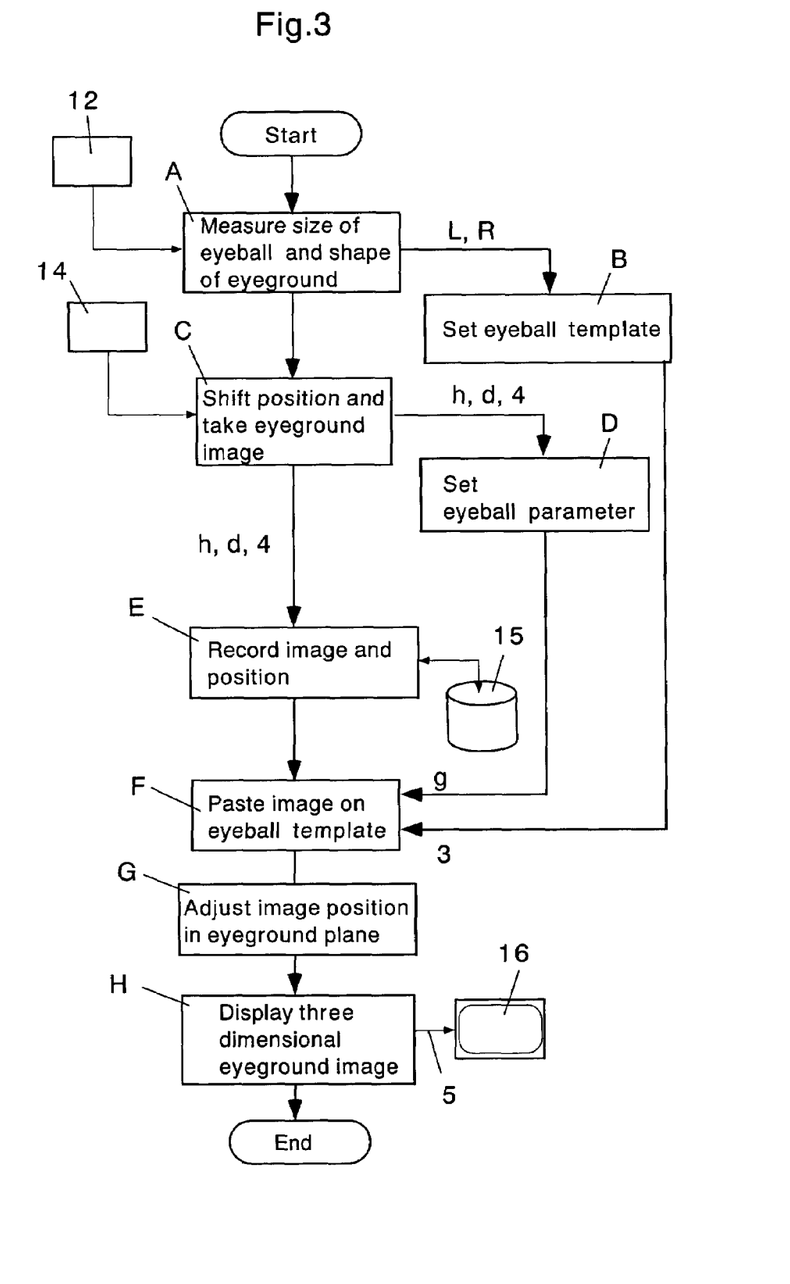
FIG. 3 is a flow chart showing the methods of the present invention.
Figure 4:
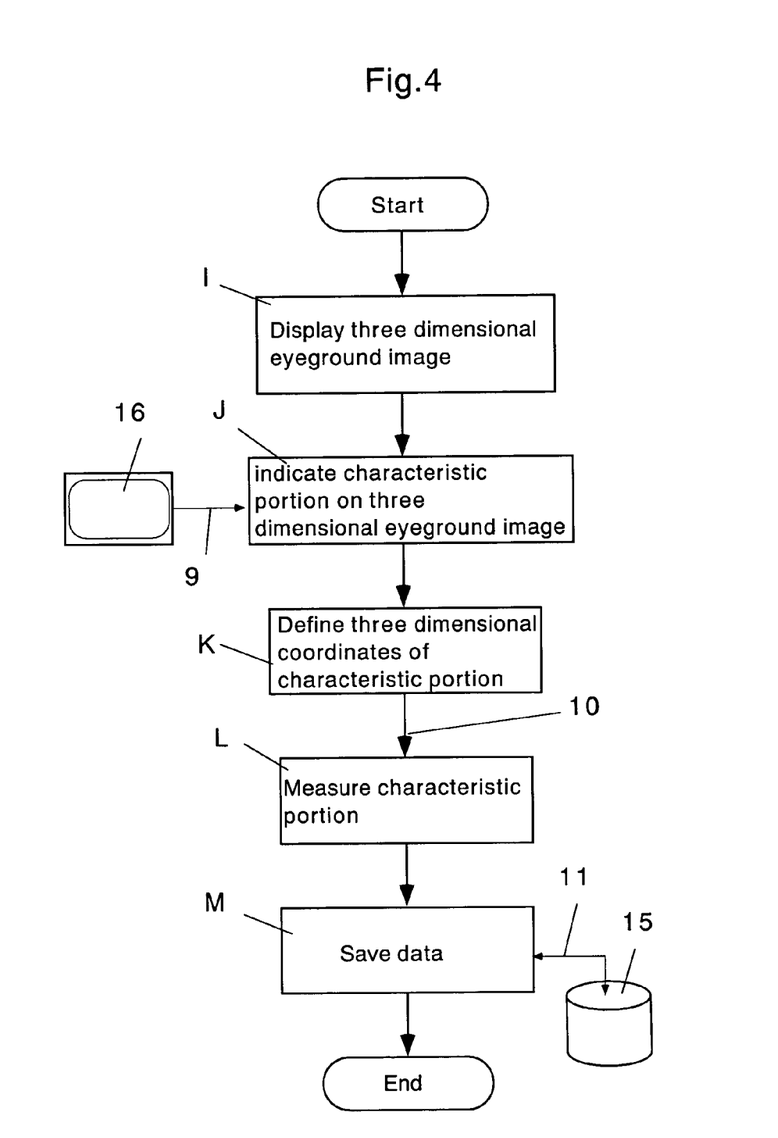
FIG. 4 is another flow chart that shows the methods of the present invention.

FIG. 3 is a flow chart showing the methods of the present invention, and FIG. 4 is another flow chart showing the same.

Referring to FIG. 3, the methods of the present invention include shape measuring step (A), eyeball setting step (B), eyeground image taking step (C), parameter setting step (D), image/position recording step (E), image pasting step (F), image positioning step (G) and three dimensional image displaying step (H).

In the shape measuring step (A), the measuring device 12 measures the size L of eyeball 1 (length from the surface of cornea to the eyeground) and the shape R of eyeground 2 (radius of curvature at the eyeground).

The size L of eyeball 1 at least includes the length from the surface of cornea to the eyeground. The shape R of eyeground 2 also covers at least the radius of curvature at the eyeground. The measuring device 12 is, for example, an ultrasonic sensor that scans at least 3 points per image of an eyeground, or irradiates ultrasonic beams to precisely scan the sizes and shapes of the eyeball 1 as a whole and the eyeground 2.

Figure 5:
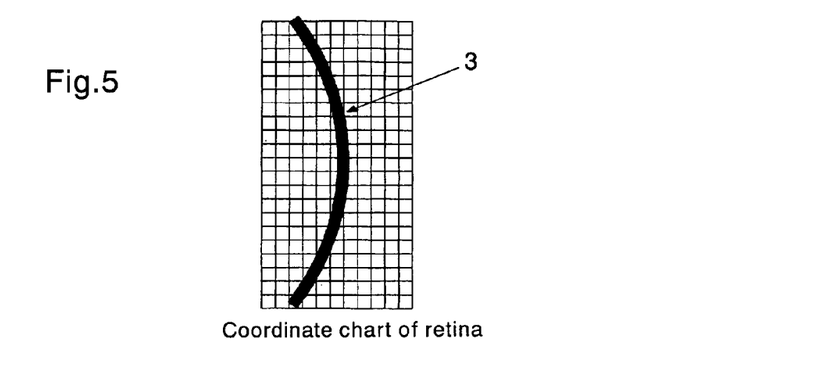
FIG. 5 is a coordinate chart of an eyeground (retina).

In the eyeball setting step (B), an eyeball template 3 is set based on measured size L and shape R. This setting is achieved virtually on the computer. That is, the coordinate diagram of the eyeground 2 including retina, as shown in FIG. 5, is created three dimensionally.

In the eyeground image taking step (C), as shown in FIGS. 2A, 2B, 8A, and 8B, imaging positions of eyeground 2 are shifted each time by a predetermined amount d, and the eyeground including superimposed portions d are photographed a number of times.

In this imaging operation, first a number of images are shot at positions slightly displaced from each other, and according to deviations between the images, an eyeball parameter g that represents the positional relationship between the eyeground and a image from position H on the image 4 at a superimposed portion is obtained in the parameter setting step (D). For example, as shown in FIG. 2B, if a unique point A of the eyeground 2 is displaced by ΔH on the image 4 when the patient stares at 2 from points T, T', provided the 2 points T, T' are known, the eyeball parameter g, which shows the positional relationship between the eyeground and the image, can be obtained from the above mentioned equations (1) to (3).

In the image/position recording step (E), image 4 photographed in the eyeground image taking step (C) and the related positional relationship between the eyeball 1 and the imaging device 14 are recorded in a recording medium 15.

Figure 6:
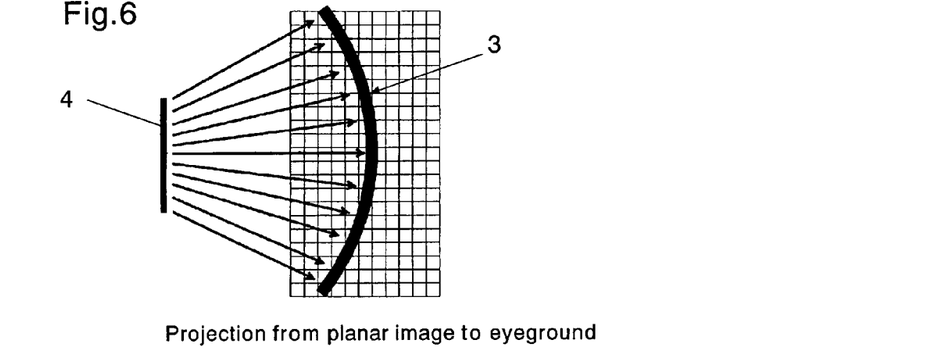
FIG. 6 is a schematic diagram showing a projection from a planar image to the eyeground.
Figure 7:
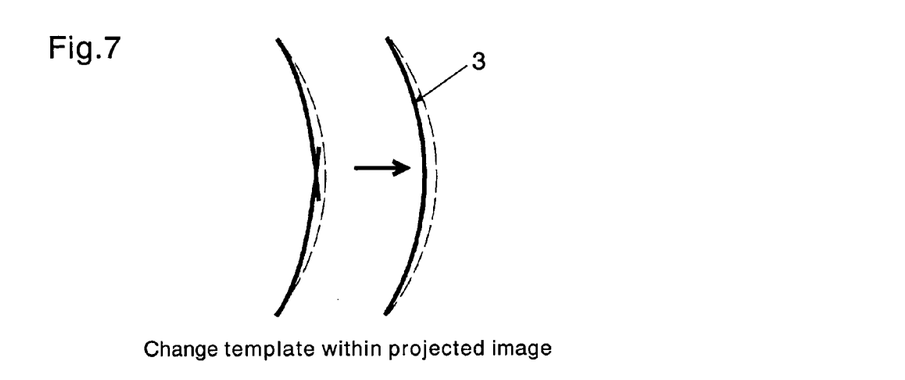
FIG. 7 is a figure that shows the change of a template in a projection image.
Figure 8A:
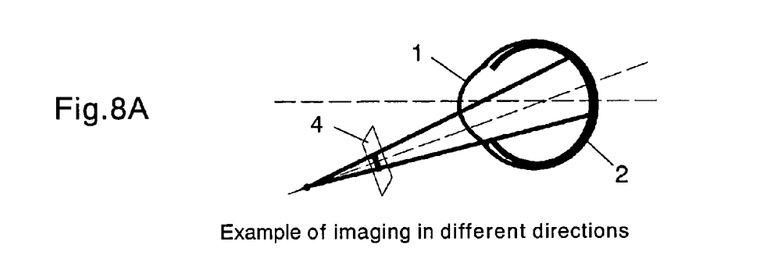
FIGS. 8A and 8B show example of photo that were shot in different directions.
Figure 8B:
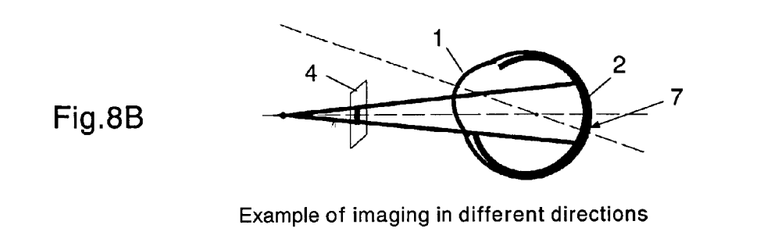

In the eyeground image taking step (C), as shown in FIGS. 8A and 8B in continuation, the imaging positions of the eyeground 2 are shifted by a predetermined amount h, and the eyeground including superimposed portions D is photographed a number of times. Next, as shown in FIG. 6, in the image pasting step (F), a number of images are pasted on the eyeball template 3 according to the eyeball parameter g. At that time, as shown in FIG. 7, the template on a projected image should be changed to the eyeball template 3 set in the eyeball setting step (B).

In the image positioning step (G), the positions of eyeground images 8 are adjusted appropriately within the plane of the eyeground 2 at the related points 7 in superimposed portions d (papilla, blood vessels, nerves, etc. at the eyeground).

In the three dimensional image displaying step (H), a three dimensional eyeground image 5 on the eyeball template 3 is displayed on a display device 16 (for instance, a CRT display). It is also possible to use a three dimensional display, CAVE or other devoted VR device (virtual reality device). The achieved three dimensional model can be easily three dimensionally visualized on a PC by converting the format to VRML etc.

According to the aforementioned methods of the present invention, in the shape measuring step (A), the measuring device 12 measures the size L of eyeball 1 (length from the surface of the cornea to the eyeground) and the shape R of eyeground 2 (radius of curvature at the eyeground), so even if the eyeball is deformed from a precision sphere, a precise eyeball template 3 can be set in the eyeball setting step (B).

As the eyeground, including superimposed portions d, is photographed by shifting the imaging positions each time by a predetermined amount h in the eyeground image taking step (C), an eyeball parameter g that shows the positional relationship between the eyeground and a image (for instance, CCD in the imaging device) according to the position H on the image 4 in a superimposed portion, can be ascertained in the parameter setting step (D).

Moreover, in the eyeground image taking step (C), the eyeground including superimposed portions d is photographed by shifting the imaging positions each time by the predetermined amount h, and a number of images taken are pasted on the eyeball template based on the eyeball parameter g in the image pasting step (F), thus a three dimensional image of the eyeground can be produced precisely and displayed on a display device 16 in the three dimensional image displaying step (H), to help unspecialized physicians and patients understand the clinical situation.

As shown in FIG. 4, the methods of the present invention further include three dimensional image displaying step (I), characteristic portion indicating step (J), three dimensional coordinate defining step (K), characteristic portion measuring step (L) and data saving step (M).

The three dimensional image displaying step (I) is substantially the same as the three dimensional image displaying step (H), wherein a three dimensional image of the eyeground is displayed on a display device 16.

Figure 10:
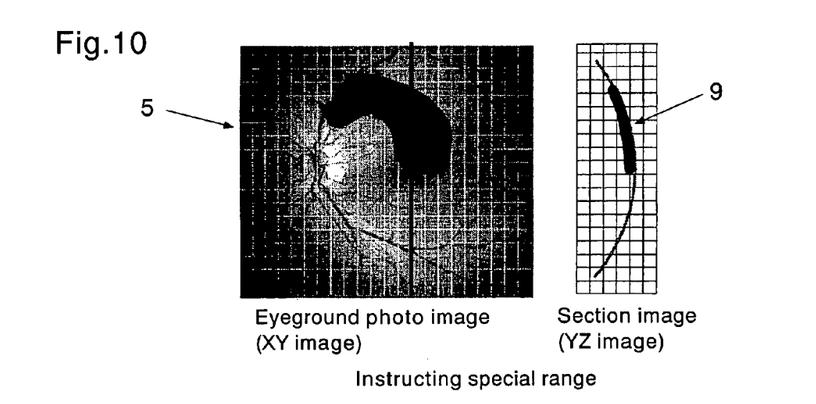
FIG. 10 includes an image in an intermediate tone on a display and its sectional view showing an indicated example in a specified area.

In the characteristic portion indicating step (J), a characteristic portion 9 on the three dimensional eyeground image 5 is displayed on the display device 16 (CRT etc.). Such an indicateion is given by enclosing the characteristic portion 9 on a two dimensional display device such as CRT display, using an input device such as a mouse, as shown in FIG. 10.

In the three dimensional coordinate defining step (K), three dimensional coordinates 10 are obtained from two dimensional coordinates designated by the characteristic portion as indicated. In the characteristic portion measuring step (L), the size of the characteristic portion is measured. These steps K and L are processed automatically by the computer.

In the data saving step (M), measured data 11 (three dimensional coordinates 10 and sizes of characteristic portions) are saved in a storage medium 15. The storage medium 15 may be either tape, drum, hard disk, CD, or any other storage device known in the prior art.

Using any of the above mentioned methods, three dimensional coordinates 10 of indicated characteristic portions can be obtained in the characteristic portion indicating step (J); furthermore, in that step, the sizes of characteristic portions can be measured, and based on three dimensional images, the sizes and the positions of pathological portions such as abnormal blood vessels, retina detachment and tumors can be converted into quantitative data.

By saving measured data (11) to the storage medium (15), the data can be used as time dependent data of the patient or in an epidemic database.

In addition, the above mentioned methods can be implemented by means of a program with the computer and a storage medium that stores the program and can be read by the computer.

Preferred Embodiments

Preferred embodiments of the present invention are described below.

Figure 11:
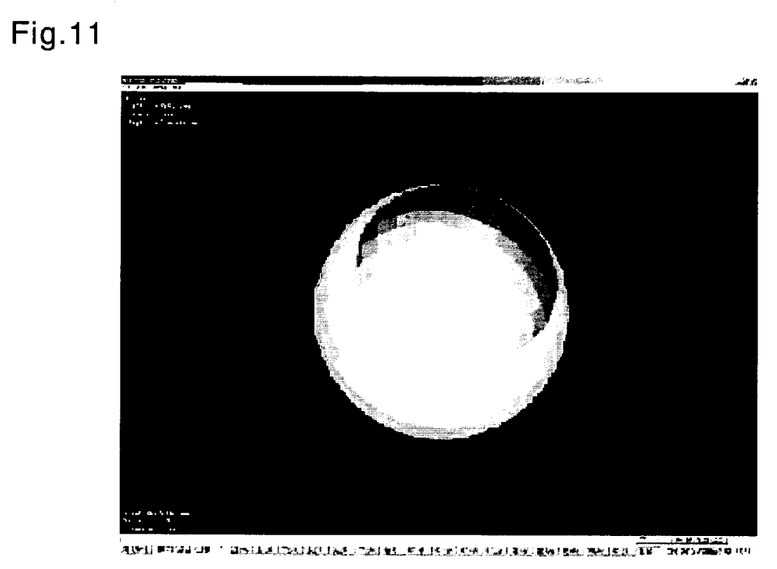
FIG. 11 is an image in an intermediate tone on a display that shows an embodiment of the eyeball template.

FIG. 11 is an image on a display, showing an embodiment of the eyeball template in an intermediate tone. This embodiment is an example of a normal eyeball, and the eyeball can be regarded forming a spherical surface. In fact, the sizes and the shapes of eyeballs vary by person; a patient having strong near or far sight, is known to have eyeballs that are deformed from a perfect sphere. The present invention is characterized in that based on the size L of the eyeball 1 and the shape R of the eyeground 2, measured in the shape measuring step (A), a precise eyeball template 3 is set in the eyeball setting step (B).

Figure 12:
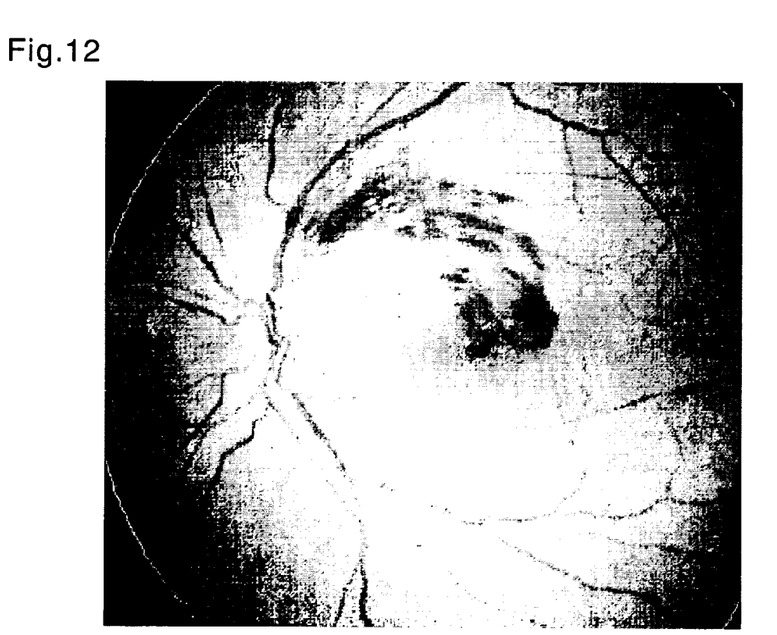
FIG. 12 is an image in an intermediate tone on the display showing an example of an eyeground photo.

FIG. 12 is an image on a display, showing an example of an eyeground photo in an intermediate tone. Obviously, the field of view in this photo is narrow at about 50 degrees, so it is understood that even a specialized physician cannot easily make a precise diagnosis from this one photo.

Figure 13:
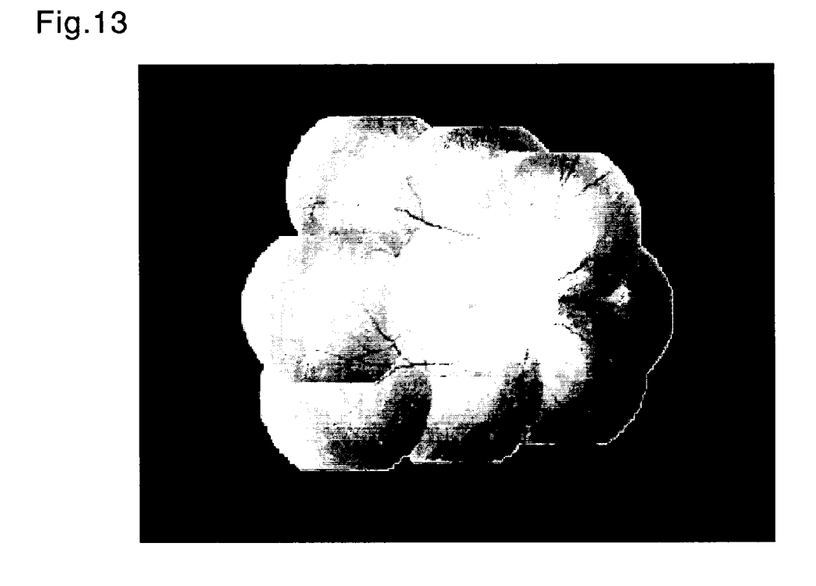
FIG. 13 is an image in an intermediate tone on the display showing a three dimensional eyeground image.
Figure 14:
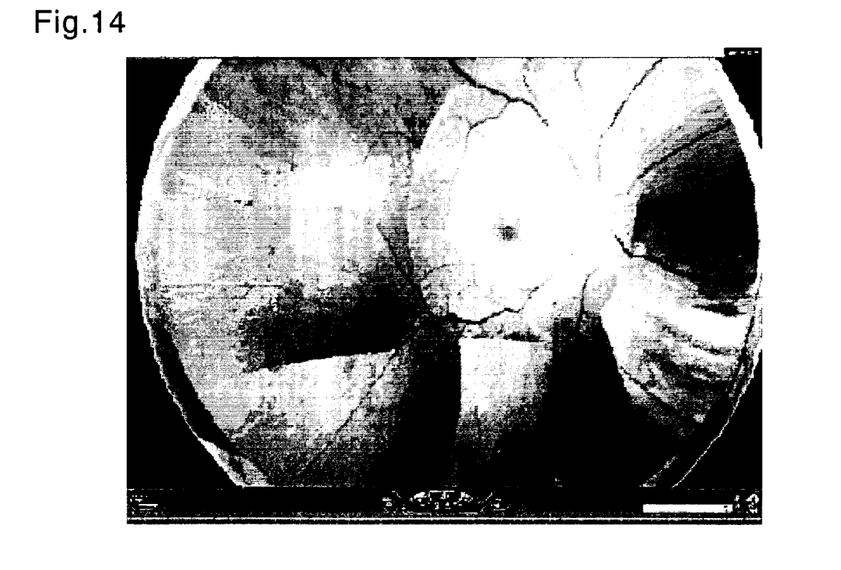
FIG. 14 is an image in an intermediate tone on the display showing another three dimensional eyeground image.

FIGS. 13 and 14 show images on a display, that is, examples of three dimensional eyeground images in an intermediate tone. FIG. 13 shows a three dimensional eyeground image 5 consisting of a number of eyeground photos (9 photos in this example) pasted on an eyeball template; actually, the field of view was changed in various directions on a computer CRT from inside the eyeground, and the eyeground was displayed stereoscopically.

For FIG. 14, the eyeground image 8 was positioned more precisely than in FIG. 13, in the image positioning step (G); in the same way as for FIG. 13, the field of view can be changed freely from inside the eyeball on CRT of a computer, and the eyeground can be displayed three dimensionally.

As described above, according to the present invention, information on an eyeground having a three dimensional structure is converted into images, that is, two dimensional information, when the eyeground of the eyeball is photographed. Although these images alone cannot form a three dimensional model of the eyeground, the three dimensional model composed uses most of the features of the eyeground images.

In practice, based on eyeground images of a patient and the size of an eyeball of the patient, a three dimensional model is constructed by virtually projecting images onto the eyeball and adding other one dimensional information in the direction of depth to the two dimensional images.

The three dimensional model thus constructed can be displayed stereoscopically using a computer graphic (CG) method. The model visualized helps to obtain informed consent because the patient can understand the construction of the eyeground without requiring any special expertise.

In addition, the three dimensional model thus formed can be measured; therefore, based on this three dimensional model, the location of damaged blood vessels, range of retina detachment, and tumors can be designated by physician, engineer, or automated diagnostic system, and its three dimensional coordinates can be ascertained. More explicitly, three dimensional coordinates can easily be calculated from the information on images projected two dimensionally (on the monitor) and visualized, by assigning a two dimensional location using a mouse etc.

From the three dimensional coordinates determined, it is also possible to define numerical data such as volumes of blood vessels and retina detached location, and their areas and shapes on the retina. With images obtained by a conventional eyeground camera, the necessary dimensions cannot be easily measured because magnification scales differ between surroundings and center of image. However, using the methods of the present invention, numerical data of such dimensions can be easily obtained because a three dimensional model is constructed. These numerical data such as for areas can be collated with time dependent data of the patient, so therapy criteria such as the progress of a disease can be presented. Also, a database can be constituted by gathering data from many patients, thereby epidemic data including diseases (frequently occurring locations, relationship with ages) can be provided. Moreover, it is also possible to configure basic data for a computer simulated analysis of a disease, which is expected to be developed further in the future.

The above mentioned methods and apparatus for displaying an eyeground three dimensionally and measuring related coordinates enable the precise production of three dimensional images of the eyeground, even if the eyeball is deformed from being a perfect sphere, so the methods and the apparatus provide great advantages such as presenting quantitative data on sizes and locations of pathologic locations of abnormal blood vessels, retina detachment, tumors, etc. based on the aforementioned three dimensional images, and use the data for time dependent therapy on the patient and in an epidemic database.

Although the present invention has been described referring to several preferred embodiments, it should be understood that the scope of rights covered by the present invention is not limited only to these embodiments. Conversely, the scope of rights of the present invention should include all modifications, corrections, and similar entities included in the claims attached.

The invention claimed is:

1. A method of three dimensionally displaying an eyeground and measuring the coordinates thereof, comprising the steps of:

(A) measuring a length from surface of a cornea to the eyeground of an eyeball and radii of curvatures at a plurality of positions on the eyeground using a measuring device;

(B) setting an eyeball template according to the measured length and radii;

(C) taking images of the eyeground including superimposed portions d by shifting imaging positions by a predetermined amount H;

(D) obtaining an eyeball parameter g that represents a positional relationship between the eyeground and images according to positions H of superimposed portions on the images;

(E) pasting a number of images on the eyeball template according to the eyeball parameter g; and (F) displaying three dimensional eyeground images from the eyeball template on a display device.

2. The method of three dimensionally displaying an eyeground and measuring the coordinates thereof, specified in claim 1, further comprising the step of (G) recording images taken in eyeground image taking step (C) and the positional relationship between the eyeball and the imaging device corresponding to each image.

3. The method of three dimensionally displaying an eyeground and measuring the coordinates thereof, specified in claim 1, wherein the superimposed portions d further comprises corresponding points, and the method further comprises the step of (G) adjusting positions of eyeground images on a plane of the eyeground according to the corresponding points in the superimposed portions d.

4. The method of three dimensionally displaying an eyeground and the measuring coordinates thereof, specified in claim 1, further comprising the steps of (G) indicating characteristic portions on three dimensional eyeground images shown on the display device;

(H) obtaining three dimensional coordinates of indicated portions on the eyeground images shown on the display device;

(I) measuring sizes of the indicated portions; and (J) storing measured data in a recording medium.

5. A computer readable storage medium that stores a program for displaying an eyeground three dimensionally and measuring the coordinates thereof, to operate the computer to execute the steps of:

(A) measuring a length from surface of a cornea to the eyeground of an eyeball and radii of curvatures at a plurality of positions on the eyeground;

(B) setting an eyeball template according to the measured length and radii;

(C) taking images of the eyeground including superimposed portions by shifting the imaging positions by a predetermined amount;

(D) obtaining an eyeball parameter that represents a positional relationship between the eyeground and images;

(E) pasting a number of images on the eyeball template according to the eyeball parameter; and (F) displaying three dimensional eyeground images on the eyeball template.

6. A method of three dimensionally displaying an eyeground and measuring the coordinates thereof, comprising:

a shape measuring step (A) in which a length from surface of a cornea to the eyeground of an eyeball and radii of curvatures at a plurality of positions on the eyeground are measured using a measuring device;

an eyeball setting step (B) for setting an eyeball template according to the measured length and radii;

an eyeground image taking step (C) for taking images of the eyeground including superimposed portions d by shifting imaging positions by a predetermined amount H;

a parameter setting step (D) for obtaining an eyeball parameter g that represents the positional relationship between the eyeground and images according to positions H of the superimposed portions on the images;

an image pasting step (F) for pasting a number of images on the eyeball template according to the eyeball parameter g; and a three dimensional image displaying step (H) for displaying three dimensional eyeground images from the eyeball template on a display device.

7. A computer readable storage medium that stores a program for displaying an eyeground three dimensionally and measuring the coordinates thereof, to operate the computer to execute a shape measuring step (A) in which a length from surface of a cornea to the eyeground of an eyeball and radii of curvatures at a plurality of positions on the eyeground are measured using a measuring device;

an eyeball setting step (B) for setting an eyeball template according to the measured length and radii;

an eyeground image taking step (C) for taking images of the eyeground including superimposed portions by shifting the imaging positions by a predetermined amount;

a parameter setting step (D) for obtaining an eyeball parameter that represents the positional relationship between the eyeground and images;

an image pasting step (F) for pasting a number of images on the eyeball template according to the eyeball parameter; and a three dimensional image displaying step (H) for displaying three dimensional eyeground images on the eyeball template.

* * * * *